United States Patent [19]

Sauerbier et al.

[11] Patent Number: 4,952,575
[45] Date of Patent: Aug. 28, 1990

[54] SOLUTIONS OF OXAPHOSPHORINS HAVING IMPROVED STABILITY AND PROCESS FOR THE PREPARATION THEREOF

[75] Inventors: Dieter Sauerbier, Werther; Klaus Molge, Bielefeld; Werner Weigert, Bielefeld; Otto Issac, Hanau, all of Fed. Rep. of Germany

[73] Assignee: Asta Pharma Aktiengesellschaft, Frankfurt am Main, Fed. Rep. of Germany

[21] Appl. No.: 307,230

[22] Filed: Feb. 6, 1989

Related U.S. Application Data

[63] Continuation of Ser. No. 72,454, Jul. 13, 1987, abandoned.

[30] Foreign Application Priority Data

Jul. 11, 1986 [DE] Fed. Rep. of Germany ....... 3623369

[51] Int. Cl.⁵ .............................................. A61K 31/66
[52] U.S. Cl. ..................................................... 514/110
[58] Field of Search .......................................... 514/110

[56] References Cited

PUBLICATIONS

Chemical Abstracts 105:12015h (1986) Abstracting Ziekenhuisfarmacie 1985 1(2) 57–58 (Weth).
Websters 3rd New International Dictionary, p. 74, 1988.
McGraw-Hill Dictionary of Scientific and Technical Terms 4th Edition, 1989, p. 81.
Chemical Abstracts, vol. 105, Ref.: 12015h.

*Primary Examiner*—Jerome D. Goldberg
*Attorney, Agent, or Firm*—Cushman, Darby & Cushman

[57] ABSTRACT

Solutions comprising oxazaphosphorins having the general formula

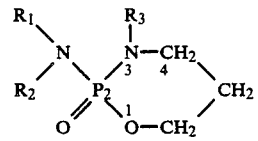

wherein $R_1$, $R_2$ and $R_3$ are radicals and at least two of said radicals are 2-chloroethyl and/or 2-mathanesulfonyloxyethyl and the remaining radical is selected from hydrogen, methyl and ethyl; and about 80% to about 100% (v/v) ethanol; wherein the oxazaphosphorin concentration is about 10% to about 70% (w/v); and a process for the preparation thereof.

6 Claims, No Drawings

SOLUTIONS OF OXAPHOSPHORINS HAVING IMPROVED STABILITY AND PROCESS FOR THE PREPARATION THEREOF

BACKGROUND OF THE INVENTION

Oxazaphosphorins belong to the group of alkylating cytostatic agents employed in the treatment of tumour diseases.

Therapeutic administration of oxazaphosphorins typically is by means of peroral and parenteral formulations. The major proportion of parenteral applications is carried out by way of infusions. As a result of the limited stability of oxazaphosphorins in aqueous solution, ready-to-use injectable solutions which can be stored have not been known until now. Parenteral formulations as of the present time tend to consist of injection vials which contain the differing doses of active ingredients in dry substance form, from which the injectable solution is prepared just before administration.

In the case of an oxazaphosphorin such as cyclophosphamide, the dry substance for parenteral application may, for example, consist of a pathogen-free mixture of crystalline cyclophosphamide monohydrate and salt. There are, however, considerable disadvantages associated with the use of such a pathogen-free crystalline mixture as compared with a ready-to-use injectable solution. Thus, even during preparation of the active ingredient, for example on crystallization, during centrifuging of the crystals, during drying, grinding and mixing with the sterile salt, which is also laborious to prepare, it is necessary to work under sterile and aseptic conditions. Finally, the finished mixture must be filled under sterile conditions. There is a always a danger of contamination by particles or microbes during this laborious procedure.

In addition, even if every care is taken during preparation, one cannot avoid the formation of differently sized crystals, so that the preparation of cyclophosphamide solutions using dry substance in injection vials is a very time-consuming procedure. In particular, in clinics and hospitals this involves the nursing staff in additional effort which is no longer warranted.

Furthermore, the exposure of the nursing staff in the course of their work, during the making-up of solutions of potentially carcinogenic cytostatic agents should be taken into consideration and contamination of the nursing staff should therefore be avoided as far as possible. During the preparation of solutions from dry substance it cannot with certainty be excluded that such particles of active ingredient could be inhaled.

For the reasons stated above, there is a need for an oxazaphosphorin formulation for parenteral administration which is easy to handle. Such a formulation should as far as possible rule out any danger for the nursing staff and, last but not least, permit economically priced therapy.

The preparation of directly injectable stable aqueous or water containing oxazaphosphorin solutions is, however, not possible owing to the instability of oxazaphosphorins as a result of hydrolytic decomposition.

It has now surprisingly been found that the non-aqueous solutions of the present invention display excellent stability and are capable of being stored for a long time. The solutions according to the present invention can be diluted in a simple manner for parenteral administration with water, Ringer's solution or similar infusion liquids, whereby the dilution should generally be carried out so that the maximum solvent or ethanol concentration is not above 10%.

SUMMARY OF THE INVENTION

The present invention, in one aspect, provides solutions, which display excellent stability, and comprise oxazaphosphorins having the general formula

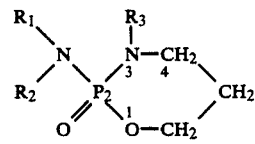

wherein $R_1$, $R_2$ and $R_3$ are radicals and at least two of said radicals are 2-chloroethyl and/or 2-methanesulfonyloxyethyl and the remaining radical is selected from hydrogen, methyl and ethyl; and about 80% to 100% ethanol, wherein the oxazaphosphorin concentration is 10 to 70 percent by weight.

In another aspect, the invention provides a process for the preparation of solutions, comprising: dissolving said oxazaphosphorins in about 80% to about 100% (v/v) ethanol, at a temperature from about 15° C. to about 40° C., to an oxazaphosphorin concentration of from about 10% to about 70% (w/v), by dissolving about 10g to 150g oxazaphosphorin per 100 ml of solvent; wherein said oxaza-phosphorins have the general formula

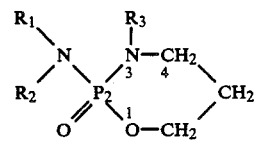

wherein $R_1$, $R_2$ and $R_3$ are radicals and at least two of said radicals are 2-chloroethyl and/or 2-methanesulfonyloxyethyl, and the remaining radical is selected from hydrogen, methyl and ethyl.

In still another aspect, a storable sealed container, such as an ampoule containing a single dosage of oxazaphosphorin solution, having an ethanol concentration of 10% or less, wherein said solution is prepared according to the method described hereinabove, is provided.

DETAILED DESCRIPTION OF THE PRESENTLY PREFERRED EXEMPLARY EMBODIMENT

Oxazaphosphorins are alkylating cytostatic agents employed in the treatment of tumor diseases and are therapeuticaly administered by means of peroral and parenteral formulations. The oxazaphosphorin solutions of the present invention are particularly suitable for use as additions to infusions. The inventive solutions may, for example, be transferred directly from an ampoule into the infusion solution.

The solutions according to the present invention possess a number of advantages as compared to solutions which are prepared from sterile powders or lyophilizates immediately before use: they, are less likely to be contaminated by particles or microbes, since one can, for example, filter immediately before filling;

permit the simple removal of aliquot amounts in a simple manner whereby the amount of active ingredient is always uniform as opposed to the variations in respect of the active ingredient in the case of a dry filling;

render the dissolution step superfluous and may be used immediately;

contribute to the safety of the nursing staff; and are more economical to prepare.

The solutions according to the present invention may be prepared by dissolving the oxazaphosphorins in about 80% to about 100% (v/v) ethanol. The designation "v/v", as used herein, shall mean the percent volume by volume, or the number of milliliters of substance in 100 milliliters of end product. Preferably the concentration of ethanol used in preparing the solutions is from about 90% to about 100%, while the most preferred ethanol concentration is from about 94% to about 98% (v/v). Therefore, absolute ethanol is quite suitable in the preparation of these solutions. Other physiologically acceptable solvents in which the oxazaphosphorin is stable may be used. However, trials carried out with the physiological solvents the glycofurol, polyethylene glycol 300, polyethylene glycol 400, 1,2-propylene glycol, 1,3-butylene glycol, showed the active ingredients as much less stable in these agents, despite the absence of any water content, the occurrence of discoloration and such solutions therefore could not be used as storage-stable pharmaceutical formulations.

Once prepared, the solutions are diluted, such that the maximum ethanol concentration is not above 10%, prior to parenteral administration. Suitable diluents include water, Ringer's solution and other similar infusion liquids.

Suitable oxazaphosphorins are those having the general formula

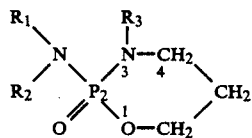

wherein $R_1$, $R_2$ and $R_3$ are radicals and at least two of said radicals are 2-chloroethyl and/or 2-methanesulfonyloxyethyl, and the remaining radical is selected from hydrogen, methyl and ethyl.

Especially suitable oxazaphosphorins for the present invention and those of therapeutic importance, are cyclophosphamide and ifosfamide. The chemical name for cyclophosphamide is 2-[bis-(2-chloroethyl)-amino]tetrahydro-2H-1, 3, 2-oxazaphosphorin-2-oxide and ifosfamide is 2-(chloroethylamino)-3-2(2-chloroethyl)-tetraphydro-2H-1, 3, 2-oxazaphosphorin-2-oxide.

The oxazaphosphorins are preferably used in crystalline form, especially a fine crystalline form. However, it is also possible to use amorphous, semi-solid or oily forms of the oxazaphosphorins. The oxazaphosphorins can also be used in the form of lyophilizates.

Generally, from about 10g to 150g oxazaphosphorin are used for every 100 ml of solvent. Preferably about 20g to 80g oxazaphosphorin are used per 100 ml of solvent and most preferred is about 30g to about 40g. The concentration of the oxazaphosphorin in the solutions according to the present invention is generally about 10% to about 70% (w/v), about 15% to 50% (w/v) being preferred, and about 20% to about 30% (w/v) most preferred. As used herein, the designation "w/v" means the percent content weight by volume or the number of grams of a substance in 100 milliliters of end product.

The dissolution is typically carried out at temperatures between about 15° C. and about 40° C., preferably between about 24° C. and about 26° C., and most preferably between about 19° C. and about 21° C.

Dissolution may be carried out under stirring or similar agitation of the solvent.

The following suitable concentrations (w/v) for oxazaphosphorins are:

cyclophosphamide, 10–60% preferably 15–40% and most preferred 20–30%; and ifosfamide, 10–70% preferably 15–50% and 20–30% most preferred. The solutions according to the present invention may also contain 2 or more different oxazaphosphorin active ingredients. In such cases the sum of the active ingredients is, for example 10 to 70%, preferably 15–50%, in particular 20 to 30% (w/v).

With the solutions according to the present invention where storage is carried out at 4° C. there is virtually no decomposition over a period of one year or the decomposition is no greater than 2%. Even with a storage temperature of 30° C., the solutions remain clear and colorless and without the formation of any precipitate.

The greatly improved stability of the ethanolic solutions prepared according to the present invention as compared to the, for example, aqueous solutions, may be seen from the following table:

| Annual Decomposition Rate | In Water | In 96% Ethanol |
|---|---|---|
| Cyclophosphamide at 4° C. | 25% | 1.5% |
| Cyclophosphamide at 20° C. | 97% | 15.0% |
| Ifosfamide at 4° C. | 2% | 0.02% |
| Ifosfamide at 20° C. | 20% | 0.3% |

SPECIFIC EMBODIMENTS

Example 1

Preparation of a 25% cyclophosphamide solution.

6 litres of 96% ethanol (DAB 8*) were placed in a suitable container and 2.673 kg of cyclophosphamide monohydrate were added with stirring. After dissolution of the active ingredient, the dissolution procedure took only a few minutes; the solution made was up to 10 litres (9.181 kg) using 96% ethanol.

\* DAB 8\* = Deutsches Arzneibuch, 8th edition 1 ml of this solution contained 250 mg of anhydrous cyclophosphamide.

For the preparation of ampoules containing 4 ml of solution, the solution prepared as above under aseptic conditions was filtered under sterile conditions through a membrane filter 0.22μm (Teflon filter material) and 4 ml in each case measured into colorless 5 ml ampoules in known manner under nitrogen.

1 ampoule contained 1g anhydrous cyclophosphamide.

EXAMPLE 2

Preparation of a 25% ifosfamide solution.

6 litres of 96% ethanol (DAB 8) were placed in a suitable container and 2.5 kg of ifosfamide were added with stirring. The dissolution procedure took only a few minutes. The solution was made up to 10 litres (9.025 kg) using 96% ethanol. 1 ml of this solution contained 250 mg of ifosfamide.

For the preparation of ampoules containing 8 ml of solution, the solution prepared as above was filtered under sterile conditions through a membrane filter 0.22 μm (Teflon filter material) and 8ml in each case measured into colorless 10 ml ampoules under nitrogen.

1 ampoule contained 2g ifosfamide.

While the invention has been described in connection with what is presently considered to be the most preferred embodiments, it is to be understood that the invention is not limited to the disclosed embodiment but, on the contrary is intended to cover various modification and equivalents included within the spirit and scope of the appended claims.

We claim:

1. A storable sealed vial containing a solution comprising an oxazaphosphorin having the general formula:

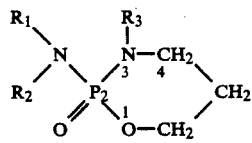

wherein $R_1$, $R_2$, and $R_3$ are radicals and at least two of said radicals are selected from the group consisting of 2-chloroethyl and 2-methanesulfonylloxyethyl and any remaining said radical is selected from the group consisting of hydrogen, methyl and ethyl; and about 80% to about 100% (v/v) ethanol; and wherein the oxazaphosphorin concentration is about 10% to about 70% (w/v).

2. A storable sealed vial as set forth in claim 1 in which the oxazaphosphorin is cyclophosphamide.

3. A storable sealed vial as set forth in claim 1 in which the oxazaphosphorin is ifosfamide.

4. A storable sealed vial as set forth in any one of claims 1, 2 or 3 in which the concentration of the ethanol is about 90–100% (v/v).

5. A storable sealed vial as set forth in any one of claims 1, 2 and 3 in which the concentration of the ethanol is about 94–98% (v/v).

6. An ampoule containing a single dose of a solution comprising an oxazaphosphorin having the general formula:

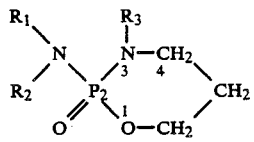

wherein $R_1$, $R_2$, and $R_3$ are radicals and at least two of said radicals are selected from the group consisting of 2-chloroethyl and 2-methanesulfonyloxyethyl and any remaining said radical is selected from the group consisting of hydrogen, methyl and ethyl; and about 80% to about 100% (v/v) ethanol; and wherein the oxazaphosphorin concentration is about 10% to about 70% (w/v).

* * * * *